United States Patent
Anderson

(10) Patent No.: US 11,167,033 B2
(45) Date of Patent: Nov. 9, 2021

(54) COMPOSITIONS AND METHODS FOR TREATING VIRAL INFECTIONS

(71) Applicant: Variation Biotechnologies Inc., Ottawa (CA)

(72) Inventor: David E. Anderson, Boston, MA (US)

(73) Assignee: Variation Biotechnologies Inc., Ottawa (CA)

( * ) Notice: Subject to any disclaimer, the term of this patent is extended or adjusted under 35 U.S.C. 154(b) by 189 days.

(21) Appl. No.: 15/810,575

(22) Filed: Nov. 13, 2017

(65) Prior Publication Data

US 2018/0256723 A1  Sep. 13, 2018

Related U.S. Application Data

(62) Division of application No. 14/371,935, filed as application No. PCT/IB2013/000453 on Jan. 11, 2013, now abandoned.

(60) Provisional application No. 61/585,971, filed on Jan. 12, 2012.

(51) Int. Cl.

| | |
|---|---|
| *A61K 47/28* | (2006.01) |
| *A61K 39/12* | (2006.01) |
| *A61K 39/39* | (2006.01) |
| *A61K 39/205* | (2006.01) |
| *A61K 47/14* | (2017.01) |
| *C12N 7/00* | (2006.01) |
| *A61K 47/24* | (2006.01) |
| *A61K 39/00* | (2006.01) |

(52) U.S. Cl.
CPC .............. *A61K 47/28* (2013.01); *A61K 39/12* (2013.01); *A61K 39/205* (2013.01); *A61K 39/39* (2013.01); *A61K 47/14* (2013.01); *A61K 47/24* (2013.01); *C12N 7/00* (2013.01); *A61K 2039/55555* (2013.01); *A61K 2039/55566* (2013.01); *C12N 2760/20134* (2013.01); *C12N 2760/20171* (2013.01); *Y02A 50/30* (2018.01)

(58) Field of Classification Search
None
See application file for complete search history.

(56) References Cited

U.S. PATENT DOCUMENTS

| | | |
|---|---|---|
| 3,952,097 A | 4/1976 | Levy |
| 4,024,241 A | 5/1977 | Levy |
| 4,349,538 A | 9/1982 | Levy |
| 4,352,884 A | 10/1982 | Nakashima et al. |
| 4,436,727 A | 3/1984 | Ribi |
| 4,537,769 A | 8/1985 | Cerini |
| 4,866,034 A | 9/1989 | Ribi |
| 4,877,611 A | 10/1989 | Cantrell |
| 4,894,228 A | 1/1990 | Purcell et al. |
| 4,912,094 A | 3/1990 | Myers et al. |
| 4,983,387 A | 1/1991 | Goldstein et al. |
| 5,057,540 A | 10/1991 | Kensil et al. |
| 5,160,669 A | 11/1992 | Wallach et al. |
| 5,250,236 A | 10/1993 | Gasco |
| 5,340,588 A | 8/1994 | Domb |
| 5,393,527 A | 2/1995 | Malick et al. |
| 5,393,530 A | 2/1995 | Schneider et al. |
| 5,549,910 A | 8/1996 | Szoka, Jr. |
| 5,567,434 A | 10/1996 | Szoka, Jr. |
| 5,653,996 A | 8/1997 | Hsu |
| 5,679,355 A | 10/1997 | Alexander et al. |
| 5,817,318 A | 10/1998 | Sia et al. |
| 5,853,753 A | 12/1998 | Maierhofer et al. |
| 5,858,368 A | 1/1999 | Smith et al. |

(Continued)

FOREIGN PATENT DOCUMENTS

| | | |
|---|---|---|
| CA | 2258907 A1 | 12/1997 |
| CA | 2767392 A1 | 1/2011 |

(Continued)

OTHER PUBLICATIONS

Ambrosch et al . . . (1997) Immunogenicity and protectivity of a new liposomal hepatitis A vaccine. Vaccine 15: 1209-1213.*
Martin, F. J. and Macdonald, R. C., Lipid vesicle-cell interactions. III. Introduction of a new antigenic determinant into erythrocyte membranes, The Journal of cell biology, 70: 515-526 (1976).
Yingzheng, Z. Biopharmaceutical Preparation, Zhejiang University Press, 1st edition, p. 73 (Jun. 2011). [No known English translation].
Alexopoulou et al.. Preparation and characterization of lyophilized liposomes with incorporated quercetin, J Liposome Res. 16(1): 17-25 (2006).
Alpan et al., The role of dentritic cells, B cells, and M cells in gut-oriented immune responses, J. Immunol., 166(8): 4843-4852 (2001).

(Continued)

*Primary Examiner* — Nianxiang Zou
(74) *Attorney, Agent, or Firm* — Choate, Hall & Stewart LLP; Rolando Medina

(57) ABSTRACT

The present disclosure provides compositions and methods useful for treating viral infections. As described herein, the compositions and methods are based on the development of immunogenic compositions that include an inactivated virus in combination with a non-ionic surfactant vesicle (NISV). In certain embodiments at least a portion of the antigen present in the composition is physically associated with the NISV. In certain embodiments the compositions are lyophilized and subsequently rehydrated after a period of storage. In certain embodiments the rehydrated compositions exhibit greater potency as compared to otherwise equivalent compositions that lack the NISV. In certain embodiments the lyophilized compositions are stored at temperatures in excess of 8° C. prior to rehydration. In certain embodiments, the rehydrated compositions exhibit greater potency as compared to otherwise equivalent compositions that lack the NISV and that were also stored at temperatures in excess of 8° C. prior to rehydration. In certain embodiments the antigen is taken from a licensed vaccine and the administered dose of antigen is less than the standard human dose for the licensed vaccine.

13 Claims, No Drawings

(56) References Cited

U.S. PATENT DOCUMENTS

| | | |
|---|---|---|
| 5,861,243 A | 1/1999 | Dietrich et al. |
| 5,876,721 A | 3/1999 | Alexander et al. |
| 5,879,703 A | 3/1999 | Fountain |
| 5,910,306 A | 6/1999 | Alving et al. |
| 5,919,480 A | 7/1999 | Kedar et al. |
| 5,948,410 A | 9/1999 | Van Scharrenburg et al. |
| 5,962,298 A | 10/1999 | Fiers et al. |
| 5,977,081 A | 11/1999 | Marciani |
| 6,005,099 A | 12/1999 | Davies et al. |
| 6,080,725 A | 6/2000 | Marciani |
| 6,090,392 A | 7/2000 | Berman |
| 6,136,606 A | 10/2000 | Chatfield |
| 6,180,110 B1 | 1/2001 | Funkhouser et al. |
| 6,207,178 B1 | 3/2001 | Westesen et al. |
| 6,235,888 B1 | 5/2001 | Pachuk et al. |
| 6,248,363 B1 | 6/2001 | Patel et al. |
| 6,287,570 B1 | 9/2001 | Foley |
| 6,290,967 B1 | 9/2001 | Volkin et al. |
| 6,303,347 B1 | 10/2001 | Johnson et al. |
| 6,344,354 B1 | 2/2002 | Webster et al. |
| 6,372,223 B1 | 4/2002 | Kistner et al. |
| 6,383,806 B1 | 5/2002 | Rios |
| 6,500,623 B1 | 12/2002 | Tung |
| 6,503,753 B1 | 1/2003 | Rios |
| 6,534,065 B1 | 3/2003 | Makin et al. |
| 6,538,123 B2 | 3/2003 | Barban |
| 6,541,003 B1 | 4/2003 | Smith |
| 6,605,457 B1 | 8/2003 | Fiers et al. |
| 6,635,246 B1 | 10/2003 | Barrett et al. |
| 6,649,410 B2 | 11/2003 | Rios |
| 6,653,130 B2 | 11/2003 | Rios |
| 6,692,955 B1 | 2/2004 | Meredith et al. |
| 6,706,859 B1 | 3/2004 | Sorensen |
| 6,740,325 B1 | 5/2004 | Arnon et al. |
| 6,743,900 B2 | 6/2004 | Burt et al. |
| 6,764,840 B2 | 7/2004 | Johnson et al. |
| 6,787,351 B2 | 9/2004 | Chen et al. |
| 6,831,169 B2 | 12/2004 | Pachuk et al. |
| 6,861,244 B2 | 3/2005 | Barrett et al. |
| 6,991,929 B1 | 1/2006 | D'Hondt |
| 7,052,701 B2 | 5/2006 | Barrett et al. |
| 7,063,849 B1 | 6/2006 | Thibodeau et al. |
| 7,067,134 B1 | 6/2006 | Kang et al. |
| 7,192,595 B2 | 3/2007 | Arnon et al. |
| 7,244,435 B2 | 7/2007 | Lai |
| 7,262,045 B2 | 8/2007 | Schwartz et al. |
| 7,316,813 B2 | 1/2008 | Eichhorn |
| 7,348,011 B2 | 3/2008 | Guntaka et al. |
| 7,361,352 B2 | 4/2008 | Birkett et al. |
| 7,399,840 B2 | 7/2008 | Burt et al. |
| 7,468,259 B2 | 12/2008 | Fiers et al. |
| 7,494,659 B2 | 2/2009 | Katinger et al. |
| 7,510,719 B2 | 3/2009 | Dang et al. |
| 7,514,086 B2 | 4/2009 | Arnon et al. |
| 7,527,800 B2 | 5/2009 | Yang et al. |
| 7,537,768 B2 | 5/2009 | Luke et al. |
| 9,610,248 B2 | 4/2017 | Anderson et al. |
| 9,849,173 B2 | 12/2017 | Anderson et al. |
| 9,907,746 B2 | 3/2018 | Anderson et al. |
| 10,736,844 B2 | 8/2020 | Anderson et al. |
| 2002/0164648 A1 | 11/2002 | Goins et al. |
| 2003/0092145 A1 | 5/2003 | Jira et al. |
| 2004/0011840 A1 | 1/2004 | Lovett |
| 2004/0022840 A1 | 2/2004 | Nagy et al. |
| 2004/0081688 A1 | 4/2004 | Del Curto et al. |
| 2005/0042230 A1 | 2/2005 | Anderson et al. |
| 2005/0095283 A1 | 5/2005 | Castor et al. |
| 2005/0169979 A1 | 8/2005 | Michaeli et al. |
| 2005/0214331 A1 | 9/2005 | Levy |
| 2006/0121105 A1 | 6/2006 | Barenholz et al. |
| 2006/0257852 A1 | 11/2006 | Rappuoli et al. |
| 2007/0142315 A1 | 6/2007 | Forsbach et al. |
| 2007/0224257 A1 | 9/2007 | Commander et al. |
| 2007/0264273 A1 | 11/2007 | Barenholz et al. |
| 2008/0057080 A1 | 3/2008 | Luke et al. |
| 2008/0131466 A1 | 6/2008 | Reed et al. |
| 2008/0145375 A1 | 6/2008 | Bembridge et al. |
| 2008/0160089 A1 | 7/2008 | Vitiello et al. |
| 2008/0181914 A1 | 7/2008 | Eichhorn |
| 2008/0213461 A1 | 9/2008 | Gill et al. |
| 2008/0268028 A1 | 10/2008 | Zurbriggen et al. |
| 2008/0286353 A1 | 11/2008 | Gregoriadis |
| 2009/0028903 A1 | 1/2009 | Hanon et al. |
| 2009/0041809 A1 | 2/2009 | Emtage |
| 2009/0081157 A1 | 3/2009 | Kornbluth et al. |
| 2009/0081254 A1 | 3/2009 | Vajdy et al. |
| 2009/0117141 A1 | 5/2009 | Torres et al. |
| 2009/0130146 A1 | 5/2009 | Broeker |
| 2009/0155309 A1 | 6/2009 | Friede et al. |
| 2009/0181078 A1 | 7/2009 | Reed et al. |
| 2009/0202620 A1 | 8/2009 | Turnell et al. |
| 2009/0232883 A1 | 9/2009 | Yoshino |
| 2010/0062071 A1 | 3/2010 | Loxley et al. |
| 2010/0080844 A1 | 4/2010 | Bacon et al. |
| 2010/0129392 A1 | 5/2010 | Shi et al. |
| 2010/0226932 A1 | 9/2010 | Smith et al. |
| 2011/0177163 A1 | 7/2011 | Diaz-Mitoma et al. |
| 2012/0156240 A1* | 6/2012 | Anderson ............... A61P 31/12 424/204.1 |
| 2012/0177683 A1* | 7/2012 | Anderson ............... A61P 31/12 424/204.1 |
| 2012/0276125 A1 | 11/2012 | Ast et al. |
| 2013/0108692 A1 | 5/2013 | Anderson et al. |
| 2013/0295165 A1 | 11/2013 | Anderson et al. |
| 2013/0323280 A1 | 12/2013 | Anderson et al. |
| 2014/0356399 A1 | 12/2014 | Anderson |
| 2015/0079077 A1 | 3/2015 | Kirchmeier et al. |

FOREIGN PATENT DOCUMENTS

| | | |
|---|---|---|
| CA | 2803282 A1 | 1/2011 |
| CN | 1169161 A | 12/1997 |
| CN | 101472563 A | 7/2009 |
| CN | 101574394 A | 11/2009 |
| EP | 0413637 A1 | 2/1991 |
| EP | 0 433242 A1 | 6/1991 |
| EP | 0489153 A1 | 6/1992 |
| EP | 729473 A1 | 9/1996 |
| EP | 1 129 723 A1 | 9/2001 |
| EP | 2 014 279 A1 | 1/2009 |
| GB | 2122204 A | 1/1984 |
| WO | WO-88/06882 A1 | 9/1988 |
| WO | WO-90/02965 A1 | 3/1990 |
| WO | WO-92/00081 A1 | 1/1992 |
| WO | WO-93/19781 A1 | 10/1993 |
| WO | WO-95/09651 A1 | 4/1995 |
| WO | WO-95/14026 A1 | 5/1995 |
| WO | WO-95/17210 A1 | 6/1995 |
| WO | WO-96/11280 A1 | 4/1996 |
| WO | WO-97/04768 A1 | 2/1997 |
| WO | WO-98/01139 A1 | 1/1998 |
| WO | WO-98/50399 A1 | 11/1998 |
| WO | WO-99/62500 A1 | 12/1999 |
| WO | WO-01/05374 A1 | 1/2001 |
| WO | WO-02/051390 A2 | 7/2002 |
| WO | WO-03/011223 A2 | 2/2003 |
| WO | WO-03/099195 A2 | 12/2003 |
| WO | WO-2005/117958 A1 | 12/2005 |
| WO | WO-2007/110776 A1 | 10/2007 |
| WO | WO-2008/153236 A1 | 12/2008 |
| WO | WO-2009/029695 A1 | 3/2009 |
| WO | WO-2009/091531 A2 | 7/2009 |
| WO | WO-2009/155489 A2 | 12/2009 |
| WO | WO-2010/033812 A1 | 3/2010 |
| WO | WO-2011/005769 A1 | 1/2011 |
| WO | WO-2011/005772 A1 | 1/2011 |
| WO | WO-2012/006367 A2 | 1/2012 |
| WO | WO-2012/006368 A2 | 1/2012 |

(56) References Cited

FOREIGN PATENT DOCUMENTS

| WO | WO-2012/097346 A1 | 7/2012 |
|----|-------------------|--------|
| WO | WO-2012/097347 A1 | 7/2012 |

OTHER PUBLICATIONS

Anderson, R.J., Properties of Cholesterol Obtained from Different Sources, J. Biol. Chem., 71:4007-418 (1927).
Andre et al., Inactivated candidate vaccines for hepatitis A, Prog. Med. Virol., 37: 72-95 (1990).
Bangham et al., Diffusion of univalent ions across the lamellae of swollen phospholipids, J. Mol. Biol. 13(1): 238-252 (1965).
Bennett, E. et al., Translational modifications to improve vaccine efficacy in an oral influenza vaccine, methods, 49: 322-327 (2009).
Bramwell, V. et al., Particulate delivery systems for vaccines: what can we expect?, The Journal of Pharmacy And Pharmacology, 58(6): 717-728 (2006).
CAS Registry 18656-38-7, Record for Dimyristoyl phosphatidylcholine, 2 pages (Nov. 16, 1984).
Chen et al., An overview of liposome lyophilization and its future potential, Journal of Controlled Release, 142: 299-311 (2010).
Chen et al., Research advances on Solid lipid nanoparticles as new drug carrier, Chinese Journal of Ethnomedicine and Ethnopharmacy, 2: 7-10 (2009).
Collins, et al., Non-Ionic Surfactant Vesicle Formulation of Stibogluconate for Canine Leishmaniasis, J. Pharm. Pharmacol. 42: 53 (1990).
Conacher, M. et al., Oral immunisation with peptide and protein antigens by formulation in lipid vesicles incorporating bile salts (bilosomes), Vaccine, 19(20-22): 2965-2974 (2001).
Cregg et al., High-Level Expression and Efficient Assembly of Hepatitis B Surface Antigen in the Methylotrophic Yeast, Pichia Pastoris, Biotechnology, 5: 479-485 (1987).
Fattovich, G. Natural history of hepatitis B, J. Hepatol., 39 Suppl 1: S50-S58 (2003).
Field, et al., Inducers of interferon and host resistance. II. Multistranded synthetic polynucleotide complexes, Proc. Natl. Acad. Sci. USA, 58(3): 1004-1010 (1967).
Gnjatic, S. et al., TLR Agonists, The Cancer Journal, 16(4): 382-391 (2010).
Harford et al., Expression of hepatitis B surface antigen in yeast, Dev. Biol. Stand., 54: 125-130 (1983).
Hassan, Y. et al., Immune responses in mice induced by HSV-1 glycoproteins presented with ISCOMs or NISV delivery systems, Vaccine, 14(17-18): 1581-1589 (1996).
Hilleman MR., Critical overview and outlook: pathogenesis, prevention, and treatment of hepatitis and hepatocarcinoma caused by hepatitis B virus, Vaccine, 21(32): 4626-4649 (2003).
Hofland, H.E.J. et al., Nonionic Surfactant Vesicles: A Study of Vesicle Formation, Characterization and Stability, Journal of Colloid and Interface Science, 161(2): 366-376, Abstract Only, 2 pages (1993).
Huckriede, A. et al., The virosome concept for influenza vaccines, Vaccine, 23 Suppl 1:S26-38 (2005).
International Search Report for PCT/IB2013/000453, 4 pages (dated Jul. 9, 2013).
Israelachvili, J.N. et al., Physical Principles of Membrane Organization, Quarterly Reviews of Biophysics, 13(2): 121-200 (1980).
Jiang et al., Advances in non-ionic surfactant based vesicles, Chinese Journal of Modern Drug Application, 1:(11): 98-101 (2007). English Translation, pp. 1-8.
Jurk, et al., Modulating Responsiveness of Human TLR7 and 8 to Small Molecule Ligands With T-rich Phosphorothiate Oligodeoxynucleotides, Eur. J. Immunol., 36(7): 1815-26 (2006).
Kasrian and Deluca, The Effect of Tertiary Butyl Alcohol on the Resistance of the Dry Product Layer During Primary Drying, Pharm. Res., 12(4): 491-495 (1995).
Kasrian and Deluca, Thermal Analysis of the Tertiary Butyl Alcohol-Water System and Its Implications on Freeze-Drying, Pharm. Res., 12(4): 484-490 (1995).
Khmelnitsky et al., Denaturation capacity: a new quantitative criterion for selection of organic solvents as reaction media in biocatalysis, European Journal of Biochem., 198: 31-41 (1991).
Kirby, and Gregoriadis, Dehydration-Rehydration Vesicles: A Simple Method for Hight Yield Drug Entrapment in Liposomes, Biotechnology, 2(11):979-984 (1984).
Kumar, G.P. et al., Nonionic surfactant vesicular systems for effective drug delivery—an overview, Acta Pharmaceutica Sinica B, 1(4): 208-219 (2011).
Lasic, D.D., Novel Applications of Lipsomes, TIBTECH, 16:307-321 (1998).
Lavanchy, The Importance of Global Surveillance of Influenza, Vaccine, 17: S24-S25 (1999).
Levy et al., Inhibition of Tumor Growth by Polyinosinic-Polycytidylic Acid, Proc. Natl. Acad. Sci. USA, 62:357-361 (1969).
Li and Deng, A novel method for the preparation of liposomes: freeze drying of monophase solutions, J. Pharm. Sci., 93(6): 1403-1414 (2004).
Mann et al., Optimisation of a Lipid Based Oral Delivery System Containing A/Panama Influenza Haemagglutinin, Vaccine, 22: 2425-2429 (2004).
Manosroi, A. et al., Characterization of vesicles prepared with various non-ionic surfactants mixed with cholesterol, Colloids and Surfaces B: Biointerfaces, 30(1-2): 129-138 (2003).
Mao et al., Further evaluation of the safety and protective efficacy of live attenuated hepatitis A vaccine (H2-strain) in humans, Vaccine, 15(9): 944-947 (1997).
McAleer et al., Human hepatitis B vaccine from recombinant yeast, Nature, 307(5947): 178-180 (1984).
Miller et al., Hepatitis C virus shares amino acid sequence similarity with pestiviruses and flaviviruses as well as members of two plant virus supergroups, Proc. Natl. Acad. Sci., 87: 2057-2061 (1990).
Mowat, A.M., Dendritic cells and immune responses to orally administered antigens, Vaccine, 23(15): 1797-1799 (2005).
Mozafari, M.R., Nanomaterials and Nanosystems for Biomedical Applications, Springer, 1-159 (2007).
Oku, et al., Effect of serum protein binding on real-time trafficking of liposomes with different charges analyzed by positron emission tomography, Biochimica et Biophysica Acta, 1280:149-154 (1996).
Pick, Liposomes With a Large Trapping Capacity Prepared by Freezing and Thawing of Sonicated Phospholipid Mixtures, Arch. Biochem. Biophys, 212(1):186-194 (1981).
Provost et al., New findings in live, attenuated hepatitis A vaccine development, J. Med. Virol., 20(2): 165-175 (1986).
Russell, DG and Alexander, J., Effective immunization against cutaneous leishmaniasis with defined membrane antigens reconstituted into liposomes, Journal of Immunology, 140(4):1274-1279 (1988).
Salager, J-L., Surfactants—Types and Uses, FIRP Booklet #E300-A, Teaching Aid in Surfactant Science & Engineering, in English, Laboratory of Formulation, Interfaces, Rheology and Processes, Universidad de Los Andes, 2:1-50 (2002).
Schalk et al., Estimation of the Number of Infectious Measles Viruses in Live Virus Vaccines Using Quantitative Real-Time PCR, Journal of Virological Methods, 117:179-187 (2004).
Schubert et al., Solvent Injection as a New Approach for Manufacturing Lipid Nanoparticles—Evaluation of the Method and Process Parameters, European Journal of Pharmaceuticals and Biopharmaceutics, 55:125-131 (2003).
Senior, J. and Radomsky, M., Liposomes for Local Sustained Drug Release, Sustained-Release Injectable Products, Chapter 7: 137-180 (Published Sep. 30, 2005).
Szoka, Jr., F. and Papahadjopoulos, D., Comparative Properties And Methods Of Preparaton Of Lipid Vesicles (Liposomes)1, Ann. Rev. Viophys. Bioeng., 9:467-508 (1980).
Tarekegn, A. et al., Niosomes in Targeted Drug Delivery: Some Recent Advances, International Journal of Pharmaceutical Sciences and Research, 1(9): 1-8 (2010).
Uchegbu, I.F. and Vyas, S.P., Non-ionic surfactant based vesicles (niosomes) in drug delivery, in International Journal of Pharmaceuticals,172:33-70 (1998).

(56) References Cited

OTHER PUBLICATIONS

Valenzuela et al., Chemical synthesis of a gene for human epidermal growth factor urogastrone and its expression in yeast, Proc. Natl. Acad. Sci. USA, 80(24): 7461-7465 (1983).

Van Hal, D. A. et al., Preparation and Characterization of Nonionic Surfactant Vesicles, Journal of Colloid and Interface Science, 178(1): 263-273 (1996).

Vangala et al., A comparative study of cationic liposome and niosome-based adjuvant systems for protein subunit vaccines: characterisation, environmental scanning electron microscopy and immunisation studies in mice, Journal of Pharmacy and Pharmacology, 58:787-799, (2006).

Varun et al., Niosomes and Liposomes—Vesicular Approach Towards Transdermal Drug Delivery, International Journal of Pharmaceutical and Chemical Sciences, 1(3): 632-644 (2012).

Verma, S. et al., Nanoparticle vesicular systems: A versatile tool for drug delivery, Journal of Chemical and Pharmaceutical Research, 2(2):496-509 (2010).

Wagner et al., Liposome Technology for Industrial Purposes, J. Drug Delivery, vol. 2011, Article ID 591325 (9 pages) (2010).

Walde et al., Enzymes Inside Lipid Vesicles: Preparation, Reactivity and Applications, Biomol. Eng., 18:143-177 (2001).

Wang et al., Solvent Injection-Lyophilization of Tert-Butyl Alcohol/Water Cosolvent Systems for the Preparation of Drug-Loaded Solid Lipid Nanoparticles, Colloids and Surfaces B: Biointerfaces, 79:254-261 (2010).

Weiner et al., Variable and hypervariable domains are found in the regions of HCV corresponding to the flavivirus envelope and NS1 proteins and the pestivirus envelope glycoproteins, Virology 180(2): 842-848 (1991).

World Health Organization, The Immunological Basis for Immunization Series, Model 7: Measles (2009).

Written Opinion for PCT/IB2013/000453, 7 pages (dated Jul. 9, 2013).

Yan et al., Recent Advances in Liposome-Based Nanoparticles for Antigen Delivery, Polymer Reviews, 47(3): 329-344 (2007).

\* cited by examiner

COMPOSITIONS AND METHODS FOR TREATING VIRAL INFECTIONS

CROSS REFERENCE TO RELATED APPLICATIONS

The present application is a divisional of U.S. application Ser. No. 14/371,935, which is the National Stage of International Application No. PCT/IB2013/000453, filed Jan. 11, 2013, which claims the benefit of U.S. provisional application Ser. No. 61/585,971, filed on Jan. 12, 2012, the contents of all of which are herein incorporated by reference in their entirety.

BACKGROUND

Many viral infections cause severe health problems and may ultimately lead to death of infected individuals. One strategy for vaccination against such viral infections involves inactivating (or "killing") a previously virulent virus and administering it to the individual. The immune system may then later recognize a virulent version of the infectious agent and can respond by neutralizing the infectious agent or by destroying cells infected by the agent. Several such inactivated vaccines have been developed e.g., for polio virus, rabies virus, and hepatitis A.

Polio virus infection can lead to minor illness which does not involve the central nervous system. However, in major illness caused by polio infection, polio virus can enter the central nervous system of an infected individual, where it infects and destroys motor neurons and may lead to muscle weakness and acute flaccid paralysis. Infection with rabies virus causes acute encephalitis in warm-blooded animals and is almost always fatal if treatment is not administered prior to the onset of severe symptoms. Hepatitis A is a serious liver disease caused by the hepatitis A virus (HAV), a virus which is transmitted from person to person, primarily by the fecal-oral route. Hepatitis A may cause symptoms including fatigue, fever, abdominal pain, jaundice, etc., which can last for as long as 6 months.

Several inactivated polio, rabies, and hepatitis A vaccines are currently licensed and have been successful in reducing the incidence of infection. However, all vaccines, including inactivated antigen vaccines, lose potency over time and the rate of potency loss is temperature-dependent. Therefore, cold-chain systems have been established to ensure that the potency of vaccines is maintained by storing them under refrigerated conditions (in most cases between 2 and 8° C.) until the point of use. Establishing a cold chain for vaccine storage and distribution is a major undertaking and maintenance is difficult. It is also apparent that, despite best efforts, cold chains do not always function as intended for many reasons, such as improperly maintained or outdated refrigeration equipment, power outages resulting in equipment failure, poor compliance with cold-chain procedures and inadequate monitoring. The result is that vaccines in the cold chain are often subjected to temperature excursions (i.e., temperatures outside of the target range).

While inactivated polio, rabies, and hepatitis A vaccines have been successful in reducing the incidence of disease worldwide, there remains a need in the art for improved vaccines that are stable and retain potency when exposed to high temperatures.

SUMMARY

The present disclosure provides compositions and methods useful for treating infections (e.g., those caused by polio virus, rabies virus, and/or hepatitis A virus). As described herein, the compositions and methods are based on the development of immunogenic compositions that include an inactivated virus in combination with a non-ionic surfactant vesicle (NISV). In certain embodiments at least a portion of the antigen present in the composition is physically associated with the NISV. In certain embodiments the compositions are lyophilized and subsequently rehydrated after a period of storage. In certain embodiments the rehydrated compositions exhibit greater potency as compared to otherwise equivalent compositions that lack the NISV. In certain embodiments the lyophilized compositions are stored at temperatures in excess of 8° C. prior to rehydration. In certain embodiments the rehydrated compositions exhibit greater potency as compared to otherwise equivalent compositions that lack the NISV and that were also stored at temperatures in excess of 8° C. prior to rehydration. In certain embodiments the antigen is taken from a licensed vaccine and the administered dose of antigen is less than the standard human dose for the licensed vaccine.

Definitions

Throughout the present disclosure, several terms are employed that are defined in the following paragraphs.

As used herein, the term "antigen" or "viral antigen" refers to a substance containing one or more epitopes that can be recognized by an antibody. In certain embodiments, an antigen can be a virus. The term "antigen" encompasses inter alia killed, but previously virulent viruses. In certain embodiments, an antigen may be an "immunogen."

As used herein, the term "immune response" refers to a response elicited in an animal. An immune response may refer to cellular immunity, humoral immunity or may involve both. An immune response may also be limited to a part of the immune system. For example, in certain embodiments, an immunogenic composition may induce an increased IFNγ response. In certain embodiments, an immunogenic composition may induce a mucosal IgA response (e.g., as measured in nasal and/or rectal washes). In certain embodiments, an immunogenic composition may induce a systemic IgG response (e.g., as measured in serum).

As used herein, the term "immunogenic" means capable of producing an immune response in a host animal against a non-host entity (e.g., a viral antigen). In certain embodiments, this immune response forms the basis of the protective immunity elicited by a vaccine against a specific infectious organism (e.g., a virus).

As used herein, the terms "therapeutically effective amount" refer to the amount sufficient to show a meaningful benefit in a subject being treated. The therapeutically effective amount of an immunogenic composition may vary depending on such factors as the desired biological endpoint, the nature of the composition, the route of administration, the health, size and/or age of the subject being treated, etc.

As used herein, the term "treat" (or "treating", "treated", "treatment", etc.) refers to the administration of a composition to a subject who has a disease, a symptom of a disease or a predisposition toward a disease, with the purpose to alleviate, relieve, alter, ameliorate, improve or affect the disease, a symptom or symptoms of the disease, or the predisposition toward the disease. In certain embodiments, the term "treating" refers to the vaccination of a subject.

DETAILED DESCRIPTION OF CERTAIN EMBODIMENTS

The present disclosure provides compositions and methods useful for treating infections (e.g., infections by polio virus, rabies virus, and/or hepatitis A virus). As described herein, the compositions and methods are based on the development of immunogenic compositions that include an inactivated virus in combination with a non-ionic surfactant vesicle (NISV). In certain embodiments at least a portion of the antigen present in the composition is physically associated with the NISV. In certain embodiments the compositions are lyophilized and subsequently rehydrated after a period of storage. In certain embodiments the rehydrated compositions exhibit greater potency as compared to otherwise equivalent compositions that lack the NISV. In certain embodiments the lyophilized compositions are stored at temperatures in excess of 8° C. prior to rehydration. In certain embodiments the rehydrated compositions exhibit greater potency as compared to otherwise equivalent compositions that lack the NISV and that were also stored at temperatures in excess of 8° C. prior to rehydration. In certain embodiments the antigen is taken from a licensed vaccine and the administered dose of antigen is less than the standard human dose for the licensed vaccine.

I. Inactivated Antigens

In some embodiments, the compositions and methods of the present disclosure may be used with one or more antigens included in a vaccine that is licensed or under development. In certain embodiments, inactivated refers to a whole killed virus. Table 1 is a non-limiting list of vaccines that are licensed or under development for polio, rabies, and Hepatitis A infections.

TABLE 1

| Vaccine | Disease |
| --- | --- |
| Polio (Ipol ®, Imovax ® Polio) | Polio |
| DTaP/IPV/HepB (Pediarix ®) | Polio |
| Rabies (BioRab ®, Imovax ® Rabies, RabAvert ®) | Rabies |
| HepA (Havrix ®, Vaqta ®) | Hepatitis A |
| HepA (Aimmugen) | Hepatitis A |
| HepA/HepB (Twinrix ®) | Hepatitis A |

In the following sections we discuss these and other exemplary antigens that could be used in compositions or methods of the present disclosure.

Polio Virus

In one aspect, the present application provides immunogenic compositions that include an inactivated poliomyelitis (also called "polio") virus. The first effective polio vaccine was first tested by Jonas Salk and is an inactivated poliovirus vaccine based on three wild virulent reference strains:

Mahoney (type 1 poliovirus)
MEF-1 (type 2 poliovirus)
Saukett (type 3 poliovirus)

The reference poliovirus strains are generally cultured in Vero cells, purified and then inactivated. It will be appreciated that any method may be used to prepare an inactivated polio virus. In general however, these methods may involve propagating a polio virus in a culture vessel containing appropriate cells (e.g., Vero cells), nutrient medium, isolating and then inactivating the antigen. While heat and formalin are commonly used to inactivate licensed polio vaccines it is to be understood that other techniques could be used, e.g., treatment with chlorine, exposure to high temperatures, etc.

Several poliovirus vaccines are currently licensed. For example, each 0.5 ml dose of Imovax® Polio contains a suspension of purified formaldehyde-inactivated polio vaccine, including Mohoney (Type 1; 40 D antigen units), MEF1 (Type 2; 8 D antigen units), and Saukett (Type 3; 32 D antigen units). Primary immunization with Imovax® Polio is usually administered as three doses, the first two doses administered 4-8 weeks apart and the third dose following 6-12 months later. A booster is currently recommended for adults and adolescents who are at greater risk of exposure to poliovirus than the general population or if more than 10 years have elapsed since the last dose of their complete vaccination series.

It will be appreciated that any poliovirus strain may be used, e.g., without limitation any of the strains described herein. In some embodiments, a single strain (e.g., subtype, serotype, and/or biotype) of poliovirus may be used in accordance with the present disclosure. In some embodiments, more than one strain (e.g., subtype, serotype and/or biotype) of poliovirus may be used in accordance with the present disclosure.

Rabies Virus

In one aspect, the present application provides immunogenic compositions that include an inactivated rabies virus. Several rabies virus vaccines are currently licensed. For example, Imovax® Rabies vaccine is a freeze-dried suspension of rabies virus prepared from WISTAR Rabies PM.WI 38 1503-3M strain. The virus is harvested from infected MRC-5 human diploid cells, concentrated by ultracentrifugation and inactivated by treatment with beta-propiolactone.

It will be appreciated that any method may be used to prepare an inactivated rabies virus. In general however, these methods may involve propagating a rabies virus in a culture vessel containing appropriate cells, nutrient medium, isolating and then inactivating the antigen. For example, heat, formalin, formaldehyde, treatment with chlorine, exposure to high temperatures, etc. may be used to inactivate rabies virus.

Each 1.0 ml dose of Imovax® Rabies contains a ≥2.5 IU rabies virus (WISTAR Rabies PM/WI 38 1503-3M strain). Primary immunization with Imovax® Rabies for individuals who have not been exposed to rabies is usually administered as three doses, the first two doses administered 7 days apart and the third dose 21 days later. A booster is currently recommended for individuals who may be repeatedly exposed to rabies virus (e.g., laboratory workers and veterinarians). Primary immunization with Imovax® Rabies for individuals who have been exposed to rabies is usually administered as five doses, one dose right immediately after exposure, followed by additional doses on the $3^{rd}$, $7^{th}$, $14^{th}$, and $28^{th}$ days.

It will be appreciated that any rabies virus strain may be used, e.g., without limitation any of the strains described herein. In some embodiments, a single strain (e.g., subtype, serotype, and/or biotype) of rabies virus may be used in accordance with the present disclosure. In some embodiments, more than one strain (e.g., subtype, serotype and/or biotype) of rabies virus may be used in accordance with the present disclosure.

Hepatitis A Virus

In one aspect, the present application provides immunogenic compositions that include an inactivated hepatitis A virus (also called "hepatitis A antigen", "HAV antigen" or "antigen" herein). All known hepatitis A vaccines include an inactivated hepatitis A virus.

It will be appreciated that any method may be used to prepare an inactivated hepatitis A virus. In general however, these methods may involve propagating a hepatitis A virus in a host cell, lysing the host cell to release the virus, isolating and then inactivating the antigen. For example, in preparing HAVRIX®, hepatitis A virus strain HM175 is propagated in MRC-5 human diploid cells. After removal of the cell culture medium, the cells are lysed to form a suspension. This suspension is purified through ultrafiltration and gel permeation chromatography procedures. The purified lysate is then treated with formalin to ensure viral inactivation (e.g., see Andre et al., *Prog. Med. Virol.* 37:72-95, 1990).

In preparing AIMMUGEN®, hepatitis A virus strain KRM0003 (established from a wild-type HAV, which had been isolated from the feces of a hepatitis A patient) is propagated in GL37 cells (a cell strain established for vaccine production from a parent cell strain of African green monkey kidney). The GL37 cells are inoculated with HAV strain KRM0003 and antigen is harvested, extensively purified and inactivated with formaldehyde.

Another example of an inactivated hepatitis A virus that is commercially available but is not a licensed vaccine is hepatitis A antigen (HAV-ag) from Meridian Life Sciences. Like HAVRIX® the Meridian HAV-ag also derives from hepatitis A virus strain HM175 but it is propagated in FRhK-4 (fetal rhesus kidney) cells. After removal of cell culture medium, the cells are lysed to form a suspension and the suspension is partially purified by gradient centrifugation and inactivated by treatment with formalin.

It will be appreciated that any hepatitis A virus strain may be used, e.g., without limitation any of the following strains which have been described in the art (and other non-human variants):

Human hepatitis A virus Hu/Arizona/HAS-15/1979
Human hepatitis A virus Hu/Australia/HM175/1976
Human hepatitis A virus Hu/China/H2/1982
Human hepatitis A virus Hu/Costa Rica/CR326/1960
Human hepatitis A virus Hu/France/CF-53/1979
Human hepatitis A virus Hu/Georgia/GA76/1976
Human hepatitis A virus Hu/Germany/GBM/1976
Human hepatitis A virus Hu/Japan/HAJ85-1/1985
Human hepatitis A virus Hu/Los Angeles/LA/1975
Human hepatitis A virus Hu/Northern Africa/MBB/1978
Human hepatitis A virus Hu/Norway/NOR-21/1998
Human hepatitis A virus Hu/Sierra Leone/SLF88/1988
Human hepatitis A virus MSM1
Human hepatitis A virus Shanghai/LCDC-1/1984

In addition, while formalin and formaldehyde are commonly used to inactivate licensed hepatitis A vaccines it is to be understood that other techniques could be used, e.g., treatment with chlorine, exposure to high temperatures, etc.

In certain embodiments it may prove advantageous to add additional steps to the traditional method for preparing an inactivated hepatitis A virus. For example, U.S. Pat. No. 6,991,929 describes including a protease treatment step (e.g., trypsin) after the virus has been propagated. This step was found to improve the removal of host cell material and yield a purer It is to be understood that any one of these licensed hepatitis A vaccines may be combined with another antigen to produce an immunogenic composition.

II. Vesicles

In general, immunogenic compositions of the present disclosure include a non-ionic surfactant vesicle (NISV). As is well known in the art, vesicles generally have an aqueous compartment enclosed by one or more bilayers which include amphipathic molecules. Any non-ionic surfactant with appropriate amphipathic properties may be used to form such a vesicle. In some embodiments, at least a portion of the antigen present in the composition is associated with the vesicle (i.e., encapsulated within an aqueous core of the vesicle and/or associated with a vesicle bilayer). These embodiments are encompassed by the term "antigen-containing vesicle." In certain embodiments an immunogenic composition may also include amounts or components of the antigen that are not associated with a vesicle.

Without limitation, examples of suitable surfactants include ester-linked surfactants based on glycerol. Such glycerol esters may comprise one of two higher aliphatic acyl groups, e.g., containing at least ten carbon atoms in each acyl moiety. Surfactants based on such glycerol esters may comprise more than one glycerol unit, e.g., up to 5 glycerol units. Glycerol monoesters may be used, e.g., those containing a $C_{12}$-$C_{20}$alkanoyl or alkenoyl moiety, for example caproyl, lauroyl, myristoyl, palmitoyl, oleyl or stearoyl. An exemplary surfactant is 1-monopalmitoyl glycerol.

Ether-linked surfactants may also be used as the non-ionic surfactant. For example, ether-linked surfactants based on glycerol or a glycol having a lower aliphatic glycol of up to 4 carbon atoms, such as ethylene glycol, are suitable. Surfactants based on such glycols may comprise more than one glycol unit, e.g., up to 5 glycol units (e.g., diglycolcetyl ether and/or polyoxyethylene-3-lauryl ether). Glycol or glycerol monoethers may be used, including those containing a $C_{12}$-$C_{20}$alkanyl or alkenyl moiety, for example capryl, lauryl, myristyl, cetyl, oleyl or stearyl. Ethylene oxide condensation products that can be used include those disclosed in PCT Publication No. WO88/06882 (e.g., polyoxyethylene higher aliphatic ether and amine surfactants). Exemplary ether-linked surfactants include 1-monocetyl glycerol ether and diglycolcetyl ether.

It is also to be understood that vesicles may also incorporate an ionic amphiphile, e.g., to cause the vesicles to take on a negative charge. For example, this may help to stabilize the vesicles and provide effective dispersion. Without limitation, acidic materials such as higher alkanoic and alkenoic acids (e.g., palmitic acid, oleic acid) or other compounds containing acidic groups including phosphates such as dialkyl phosphates (e.g., dicetylphospate, or phosphatidic acid or phosphatidyl serine) and sulphate monoesters such as higher alkyl sulphates (e.g., cetylsulphate), may all be used for this purpose. The ionic amphiphile, if present, will typically comprise, between 1 and 50% by weight of the non-ionic surfactant (e.g., 1-5%, 1-10%, 1-15%, 1-20%, 1-25%, 1-30%, 1-35%, 1-40%, 1-45%, 5-10%, 5-15%, 5-20%, 5-25%, 5-30%, 5-35%, 5-40%, 5-45%, 5-50%, 10-15%, 10-20%, 10-25%, 10-30%, 10-35%, 10-40%, 10-45%, 10-50%, 15-20%, 15-25%, 15-30%, 15-35%, 15-40%, 15-45%, 15-50%, 20-25%, 20-30%, 20-35%, 20-40%, 20-45%, 20-50%, 25-30%, 25-35%, 25-40%, 25-45%, 25-50%, 30-35%, 30-40%, 30-45%, 30-50%, 35-40%, 35-45%, 35-50%, 40-45%, 40-50%, or 45-50%).

To form vesicles, the components may be admixed with an appropriate hydrophobic material of higher molecular mass capable of forming a bi-layer (such as a steroid, e.g., a sterol such as cholesterol). The presence of the steroid assists in forming the bi-layer on which the physical properties of the vesicle depend. The steroid, if present, will typically comprise between 20 and 120% by weight of the non-ionic surfactant (e.g., 20-30%, 20-40%, 20-50%, 20-60%, 20-70%, 20-80%, 20-90%, 20-100%, 20-110%, 30-40%, 30-50%, 30-60%, 30-70%, 30-80%, 30-90%, 30-100%, 30-110%, 30-120%, 40-50%, 40-60%, 40-70%, 40-80%, 40-90%, 40-100%, 40-110%, 40-120%, 50-60%, 50-70%, 50-80%, 50-90%, 50-100%, 50-110%, 50-120%, 60-70%, 60-80%, 60-90%, 60-100%, 60-110%, 60-120%, 70-80%, 70-90%, 70-100%, 70-110%, 70-120%, 80-90%, 80-100%, 80-110%, 80-120%, 90-100%, 90-110%, 90-120%, 100-110%, 100-120%, or 110-120%).

In certain embodiments, the vesicles comprise a non-ionic surfactant, an ionic amphiphile and a steroid. In certain embodiments, the vesicles comprise 1-monopalmitoyl glycerol, dicetylphosphate and cholesterol.

In certain embodiments, the vesicles consist essentially of a non-ionic surfactant, an ionic amphiphile and a steroid. In certain embodiments, the vesicles consist essentially of 1-monopalmitoyl glycerol, dicetylphosphate and cholesterol.

In certain embodiments, the vesicles do not comprise a transport enhancing molecule which facilitates the transport of lipid-like molecules across mucosal membranes. In some embodiments, the vesicles do not comprise a "bile acid" such as cholic acid and chenodeoxycholic acid, their conjugation products with glycine or taurine such as glycocholic and taurocholic acid, derivatives including deoxycholic and ursodeoxycholic acid, and salts of each of these acids. In some embodiments, the vesicles do not comprise acyloxylated amino acids, such as acylcarnitines and salts thereof, and palmitoylcarnitines.

Methods for Making Vesicles

It will be appreciated that there are known techniques for preparing vesicles comprising non-ionic surfactants, such as those referred to in PCT Publication No. WO93/019781. An exemplary technique is the rotary film evaporation method, in which a film of non-ionic surfactant is prepared by rotary evaporation from an organic solvent, e.g., a hydrocarbon or chlorinated hydrocarbon solvent such as chloroform, e.g., see Russell and Alexander, *J. Immunol.* 140:1274, 1988. The resulting thin film is then rehydrated in bicarbonate buffer optionally in the presence of antigen.

Another method for the production of vesicles is that disclosed by Collins et al., *J. Pharm. Pharmacol.* 42:53, 1990. This method involves melting a mixture of the non-ionic surfactant, steroid (if used) and ionic amphiphile (if used) and hydrating with vigorous mixing in the presence of aqueous buffer.

Another method involves hydration in the presence of shearing forces. An apparatus that can be used to apply such shearing forces is a well-known, suitable equipment (see, e.g., PCT Publication No. WO88/06882). Sonication and ultra-sonication are also effective means to form the vesicles or to alter their particle size.

In certain embodiments, at least a portion of the viral antigen is associated with lipid vesicles (where, as used herein, the term "association" encompasses any form of physical interaction). In certain embodiments, at least a portion of the viral antigen is entrapped within lipid vesicles. Association and entrapment may be achieved in any manner. For example, in the rotary film evaporation technique, this can be achieved by hydration of the film in the presence of antigen. In other methods, the viral antigen may be associated with preformed vesicles by a dehydration-rehydration method in which viral antigen present in the aqueous phase is entrapped by flash freezing followed by lyophilization, e.g., see Kirby and Gregoriadis, *Biotechnology* 2:979, 1984. Alternatively a freeze thaw technique may be used in which vesicles are mixed with the viral antigen and repeatedly flash frozen in liquid nitrogen, and warmed to a temperature of the order of, e.g., 60° C. (i.e., above the transition temperature of the relevant surfactant), e.g., see Pick, *Arch. Biochem. Biophys.* 212:195, 1981.

In certain embodiments, vesicles for use in accordance with the present invention are prepared by a method that includes: melting the non-ionic surfactant (optionally with a steroid and/or an ionic amphiphile, collectively the "lipids") to produce a molten mixture; combining the molten mixture with an aqueous solution that includes a viral antigen; and homogenizing the resulting product. In certain embodiments, the molten mixture is are added to the aqueous solution that includes the viral antigen. In certain embodiments, aqueous solution that includes the viral antigen is added to the molten mixture.

In certain embodiments, the molten mixture and aqueous solution are combined in relative amounts and volumes that achieve a lipid concentration of at least about 2 mg/ml in the resulting product. Indeed, through experimentation and as described in the Examples, we have found that when the lipids and viral antigen are homogenized with a lipid concentration in excess of 5 mg/ml the resulting compositions tend to be more thermostable than when a lower lipid concentration is used (see Examples). In some embodiments, therefore, the present invention provides desirable compositions (specifically including thermostable compositions) comprising a viral antigen and vesicles, which compositions contain a specified lipid concentration established herein to impart particular characteristics (e.g., improved thermostability) to the compositions.

In certain embodiments, a lipid concentration of at least about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90 or 95 mg/ml is achieved. In certain embodiments, the lipid concentration is in a range of about 5 mg/ml to about 10, 11, 12, 13, 14, 15, 16, 17, 18, 19, 20, or 25 mg/ml. In certain embodiments, the lipid concentration is in a range of about 5, 6, 7, 8, 9, 10, 11, 12, 13, 14, 15 mg/ml to about 30 mg/ml. In certain embodiments, the lipid concentration is in a range of about 2 mg/ml to about 5 mg/ml, about 5 mg/ml to about 50 mg/ml, about 5 mg/ml to about 25 mg/ml, about 10 mg/ml to about 50 mg/ml, about 10 mg/ml to about 30 mg/ml, or about 10 mg/ml to about 50 mg/ml.

In some embodiments, the non-ionic surfactant (optionally with other components such as a steroid and/or an ionic amphiphile) is melted at a temperature range between 120° C. and 150° C. (e.g., between 120° C. and 125° C., between 120° C. and 130° C., between 120° C. and 140° C., between 130° C. and 140° C., between 135° C. and 145° C., or between 140° C. and 145° C.). In some embodiments, the non-ionic surfactant (optionally with other components such as a steroid and/or an ionic amphiphile) is melted at about 120° C., at about 125° C., at about 130° C., at about 135° C., at about 140° C., at about 145° C. or at about 150° C.

In some embodiments, the aqueous solution comprising a viral antigen is temperature controlled. In some embodiments, the aqueous solution comprising a viral antigen is kept at a temperature of less than about 50° C. during the step of adding (e.g., less than about 45° C., less than about 40° C., less than about 35° C., less than about 30° C., less than about 25° C., etc.). In some embodiments, the aqueous solution comprising a viral antigen is kept at a temperature range between about 25° C. and about 50° C. In some embodiments, the aqueous solution comprising a viral antigen is kept at room temperature.

In certain embodiments the vesicles are made by a process which includes steps of providing a lyophilized non-ionic surfactant (optionally with other components such as a steroid and/or an ionic amphiphile) and rehydrating the lyophilized non-ionic surfactant with an aqueous solution comprising a antigen such that antigen-containing vesicles are formed. The lyophilized non-ionic surfactant is prepared by melting the non-ionic surfactant (optionally with other components such as a steroid and/or an ionic amphiphile) to produce a molten mixture and then lyophilizing the molten mixture.

As described in more detail herein, in some embodiments, an immunogenic composition that includes a antigen formulated with vesicles may be lyophilized for future use and subsequently hydrated prior to use.

Vesicle Size and Processing

It will be appreciated that a vesicle composition will typically include a mixture of vesicles with a range of sizes. It is to be understood that the diameter values listed below correspond to the most frequent diameter within the mixture. In some embodiments >90% of the vesicles in a composition will have a diameter which lies within 50% of the most frequent value (e.g., 1000±500 nm). In some embodiments the distribution may be narrower, e.g., >90% of the vesicles in a composition may have a diameter which lies within 40, 30, 20, 10 or 5% of the most frequent value. In some embodiments, sonication or ultra-sonication may be used to facilitate vesicle formation and/or to alter vesicle particle size. In some embodiments, filtration, dialysis and/or centrifugation may be used to adjust the vesicle size distribution.

In general, vesicles produced in accordance with the methods of the present disclosure may be of any size. In certain embodiments, the composition may include vesicles with diameter in range of about 10 nm to about 10 µm. In certain embodiments, vesicles are of diameters between about 100 nm to about 5 µm. In certain embodiments, vesicles are of diameters between about 500 nm to about 2 µm. In certain embodiments, vesicles are of diameters between about 800 nm to about 1.5 µm. In some embodiments, the compositions may include vesicles with a diameter in the range of about 150 nm to about 15 µm. In certain embodiments, the vesicles may have a diameter which is greater than 10 µm, e.g., about 15 µm to about 25 µm. In certain embodiments, the vesicles may have a diameter in the range of about 0.1 µm to about 20 µm, about 0.1 µm to about 15 µm, about 0.1 µm to about 10 µm, about 0.5 µm to about 20 µm, about 0.5 µm to about 15 µm, about 0.5 wu to about 10 µm, about 1 µm to about 20 µm, about 1 µm to about 15 µm, or about 1 µm to about 10 µm. In certain embodiments, the vesicles may have a diameter in the range of about 2 µm to about 10 µm, e.g., about 1 µm to about 4 µm. In certain embodiments, the vesicles may have a diameter which is less than 150 nm, e.g., about 50 nm to about 100 nm.

Lyophilization

Liquid formulation of vaccines has been the default presentation since the introduction of vaccines. Most of the existing liquid vaccine compositions have been developed for storage under refrigeration, but not at higher temperatures, with the result that their stability may not be optimal. In some cases, licensed vaccines are currently formulated and stored as liquids. In the aqueous environment the antigens are subjected to physical and chemical degradation that may lead to inactivation and loss of potency.

As discussed above, the methods of the present disclosure may include a step of lyophilizing a solution of a non-ionic surfactant (optionally with other components such as a steroid and/or an ionic amphiphile). Lyophilization is an established method used to enhance the long-term stability of products. Enhancement of physical and chemical stability is thought to be accomplished by preventing degradation and hydrolysis. Lyophilization involves freezing the preparation in question and then reducing the surrounding pressure (and optionally heating the preparation) to allow the frozen solvent(s) to sublime directly from the solid phase to gas (i.e., drying phase). In certain embodiments, the drying phase is divided into primary and secondary drying phases.

The freezing phase can be done by placing the preparation in a container (e.g., a flask, eppendorf tube, etc.) and optionally rotating the container in a bath which is cooled by mechanical refrigeration (e.g., using dry ice and methanol, liquid nitrogen, etc.). In some embodiments, the freezing step involves cooling the preparation to a temperature that is below the eutectic point of the preparation. Since the eutectic point occurs at the lowest temperature where the solid and liquid phase of the preparation can coexist, maintaining the material at a temperature below this point ensures that sublimation rather than evaporation will occur in subsequent steps.

The drying phase (or the primary drying phase when two drying phases are used) involves reducing the pressure and optionally heating the preparation to a point where the solvent(s) can sublimate. This drying phase typically removes the majority of the solvent(s) from the preparation. It will be appreciated that the freezing and drying phases are not necessarily distinct phases but can be combined in any manner. For example, in certain embodiments, the freezing and drying phases may overlap.

A secondary drying phase can optionally be used to remove residual solvent(s) that was adsorbed during the freezing phase. Without wishing to be bound to any theory, this phase involves raising the temperature to break any physico-chemical interactions that have formed between the solvent molecules and the frozen preparation. Once the drying phase is complete, the vacuum can be broken with an inert gas (e.g., nitrogen or helium) before the lyophilized product is optionally sealed.

In some embodiments, the lyophilized product is substantially free of organic solvent(s).

Excipients such as sucrose, amino acids or proteins such as gelatin or serum albumin may be used to protect the antigen during the drying process and storage. In some embodiments, a lyoprotectant may be used to protect antigens during lyophilization. Exemplary lyoprotectants include sucrose, trehalose, polyethylene glycol (PEG), dimethyl-succinate buffer (DMS), bovine serum albumin (BSA), mannitol, sorbitol, and dextran. Any suitable amount and/or combination of lyoprotectant(s) may be used to protect the antigen. For example, as demonstrated in U.S. Pat. No. 6,290,967, the dual presence of a disaccharide (e.g., sucrose) and a 6-carbon polyhydric alcohol (e.g., a sorbitol) enhanced the stability of a vaccine composition compared to control compositions. Sucrose was added in an amount ranging from 10 to 70 grams per liter of vaccine, and sorbitol was added in an amount ranging from about 15 to 90 grams per liter of vaccine.

Rehydration

Once a solution has been lyophilized, the methods of the present disclosure may include a step of rehydrating the lyophilized product to form antigen-containing vesicles. In some embodiments, this is achieved by mixing the lyophilized product with an aqueous solution comprising a antigen. In some embodiments, this involves adding the aqueous solution to the lyophilized product.

In some embodiments, the antigen-containing vesicles contain at least about 10% of the antigen added in the step of rehydrating. In some embodiments, the antigen-containing vesicles contain at least about 20% of the antigen added in the step of rehydrating. Tn some embodiments, the antigen-containing vesicles contain at least about 30% of the antigen added in the step of rehydrating. In some embodiments, the antigen-containing vesicles contain at least about 40% of the antigen added in the step of rehydrating. In some embodiments, the antigen-containing vesicles contain at least about 50% of the antigen added in the step of rehydrating. In some embodiments, the antigen-containing vesicles contain at least about 60% of the antigen added in the step of rehydrating. In some embodiments, the antigen-containing vesicles contain at least about 70% of the antigen added in the step of rehydrating. In some embodiments, the antigen-containing vesicles contain at least about 80% of the antigen added in the step of rehydrating. In some embodiments, the antigen-containing vesicles contain at least about 90% of the antigen added in the step of rehydrating.

In some embodiments, the aqueous solution includes a buffer. The buffer used will typically depend on the nature of the antigen or antigens in the aqueous solution. For example, without limitation, a PCB buffer, an $Na_2HPO_4/NaH_2PO_4$ buffer, a PBS buffer, a bicine buffer, a Tris buffer, a HEPES buffer, a MOPS buffer, etc. may be used. PCB buffer is produced by mixing sodium propionate, sodium cacodylate, and bis-Tris propane in the molar ratios 2:1:2. Varying the amount of HCl added enables buffering over a pH range from 4-9. In some embodiments, a carbonate buffer may be used.

In some embodiments, a composition of antigen-containing vesicles may be lyophilized for future use and subsequently hydrated (e.g., with sterile water or an aqueous buffer) prior to use. In some embodiments, a composition of antigen-containing vesicles may be stored at −80° C. prior to lyophilization.

In certain embodiments, the rehydrated immunogenic composition exhibits substantially the same potency as the immunogenic composition prior to lyophilization.

In some embodiments, the rehydrated immunogenic composition exhibits at least about 50% of the potency as the immunogenic composition prior to lyophilization (e.g., at least about 55%, 60%, 65%, 70%, 75%, 80%, 85%, 90%, 95% or 99%). In some embodiments, the level of potency is based on measurements obtained using an ELISA. In some embodiments, the level of potency is based on a plaque assay measurement.

In some embodiments, the rehydrated immunogenic composition exhibits at least 1.5 fold greater potency as compared to an otherwise equivalent immunogenic composition that was formulated without NISV (e.g., at least about 2 fold, 2.5 fold, 3 fold, 3.5 fold, 4 fold or 5 fold). In some embodiments, the level of potency is based on measurements obtained using an ELISA. In some embodiments, the level of potency is based on a plaque assay measurement.

Storage

In certain embodiments, the lyophilized immunogenic composition may be stored for a period of time (e.g., days, weeks or months) prior to rehydration and administration to a subject in need thereof. In certain embodiments, the lyophilized immunogenic composition is exposed to temperatures in excess of 8° C. during storage (e.g., temperatures in excess of 10° C., 15° C., 20° C., 25° C., 30° C., 35° C., or 40° C., temperatures in the range of 10° C. to 40° C., temperatures in the range of 20° C. to 40° C., temperatures in the range of 30° C. to 40° C., temperatures in the range of 10° C. to 30° C., temperatures in the range of 20° C. to 30° C., room temperature, etc.). In certain embodiments, the lyophilized immunogenic composition is stored under conditions that are not temperature controlled.

In certain embodiments, the lyophilized immunogenic compositions are thermostable in that the potency of the immunogenic composition remains substantially unchanged during storage despite being exposed to temperatures in excess of 8° C. (e.g., temperatures in excess of 10° C., 15° C., 20° C., 25° C., 30° C., 35° C., or 40° C., temperatures in the range of 10° C. to 40° C., temperatures in the range of 20° C. to 40° C., temperatures in the range of 30° C. to 40° C., temperatures in the range of 10° C. to 30° C., temperatures in the range of 20° C. to 30° C., room temperature, etc.) for a period of 1 to 36 months or longer (e.g., 1, 2, 3, 4, 5, 6, 7, 8, 9, 10, 11, 12, 14, 16, 18, 20, 22, 24, 28, 36, or more months).

In certain embodiments, storage of the lyophilized immunogenic composition at these elevated temperatures destroys less than 20% of the potency of the antigen (e.g., less than 15%, less than 10%, less than 5%, less than 1%) as measured in an ELISA and as compared to an equivalent lyophilized immunogenic composition that was stored between 2 and 8° C. for the same time period.

In certain embodiments, the potency of the antigen post-storage is at least 1.5 fold greater than in an otherwise equivalent lyophilized immunogenic composition that was stored under the same elevated temperatures but that was formulated without NISV (e.g., at least about 2 fold, 2.5 fold, 3 fold, 3.5 fold, 4 fold or 5 fold). In some embodiments, the level of potency is based on measurements obtained using an ELISA. In some embodiments, the level of potency is based on plaque assay measurements.

In some embodiments, one or more of these potency results are obtained when the lyophilized immunogenic composition is stored at 25° C. for 1, 2, 3, 4, 5 or 6 months. In some embodiments, these results are obtained when the lyophilized immunogenic composition is stored at 15° C., 20° C., 30° C., 35° C. or 40° C. for 1 month. In some embodiments, these results are obtained when the lyophilized immunogenic composition is stored at 15° C., 20° C., 30° C., 35° C. or 40° C. for 2 months. In some embodiments, these results are obtained when the lyophilized immunogenic composition is stored at 15° C., 20° C., 30° C., 35° C. or 40° C. for 3 months. In some embodiments, these results are obtained when the lyophilized immunogenic composition is stored at 15° C., 20° C., 30° C., 35° C. or 40° C. for 4 months. In some embodiments, these results are obtained when the lyophilized immunogenic composition is stored at 15° C., 20° C., 30° C., 35° C. or 40° C. for 5 months. In some embodiments, these results are obtained when the lyophilized immunogenic composition is stored at 15° C., 20° C., 30° C., 35° C. or 40° C. for 6 months. In some embodiments, these results are obtained when the lyophilized immunogenic composition is stored at 15° C., 20° C., 30° C., 35° C. or 40° C. for 6 months, 7 months, 8 months, 9 months, 10 months, 11 months, 12 months, 14 months, 16 months, 18 months, 20 months, 22 months, 24 months, 28 months, 36 months, or longer. In certain embodiments these temperatures may be allowed to vary within a range, e.g., ±2° C.

IV. Dosage and Administration

The compositions and methods of this disclosure are useful for treating infections in humans including adults and children. In general, however, compositions and methods of the present disclosure may be used with any animal. In certain embodiments, compositions and methods herein may be used for veterinary applications, e.g., canine and feline applications. If desired, compositions and methods herein may also be used with farm animals, such as ovine, avian, bovine, porcine and equine breeds.

Compositions described herein will generally be administered in such amounts and for such a time as is necessary or sufficient to induce an immune response. Dosing regimens may consist of a single dose or a plurality of doses over a period of time. The exact amount of an immunogenic composition to be administered may vary from subject to subject and may depend on several factors. Thus, it will be appreciated that, in general, the precise dose used will be as determined by the prescribing physician and will depend not only on the weight of the subject and the route of administration, but also on the age of the subject and the severity of the symptoms and/or the risk of infection.

In certain embodiments, the antigen is taken from a licensed human viral vaccine and the immunogenic composition is administered to a human at a dose that is less than the standard human dose (e.g., in the range of 10-90%, 10-80%, 10-70%, 10-60%, 10-50%, 10-40%, 10-30%, 10-20%, 20-90%, 20-80%, 20-70%, 20-60%, 20-50%, 20-40%, 20-30%, 30-90%, 30-80%, 30-70%, 30-60%, 30-50%, 30-40%, 40-90%, 40-80%, 40-70%, 40-60%, 40-50%, 50-90%, 50-80%, 50-70%, 50-60%, 60-90%, 60-80%, 60-70%, 70-90%, 70-80%, or 80-90% of the standard human dose).

In certain embodiments the immunogenic composition is administered as a single dose. In certain embodiments the immunogenic composition is administered as more than one dose (e.g., 1-3 doses that are separated by 1-12 months).

In certain embodiments, the compositions may be formulated for delivery parenterally, e.g., by injection. In such embodiments, administration may be, for example, intravenous, intramuscular, intradermal, or subcutaneous, or via by infusion or needleless injection techniques. In certain embodiments, the compositions may be formulated for intramuscular delivery. In certain embodiments, the compositions may be formulated for subcutaneous delivery. For such parenteral administration, the compositions may be prepared and maintained in conventional lyophilized compositions and reconstituted prior to administration with a pharmaceutically acceptable saline solution, such as a 0.9% saline solution. The pH of the injectable composition can be adjusted, as is known in the art, with a pharmaceutically acceptable acid, such as methanesulfonic acid. Other acceptable vehicles and solvents that may be employed include Ringer's solution and U.S.P. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable compositions can be sterilized, for example, by filtration through a bacterial-retaining filter, or by incorporating sterilizing agents in the form of sterile solid compositions which can be dissolved or dispersed in sterile water or other sterile injectable medium prior to use.

In some embodiments, compositions described herein (e.g., antigen-containing vesicles described herein) elicit immune responses that are higher than immune responses elicited by corresponding compositions comprising antigens but lacking vesicles. In some embodiments, compositions comprising antigen-containing vesicles elicit immune responses that are at least about 10%, 20%, 30%, 40%, 50%, 60%, 70%, 80%, 90%, 100%, 125%, 150%, 175%, 200%, 250%, 500%, 750%, 1000% or more, higher than immune responses elicited by compositions comprising corresponding antigens but lacking vesicles Immune responses can be measured using known assays, such as, for example, an enzyme immune assay (EIA) such as enzyme-linked immunosorbent assay (ELISA), a radioimmune assay (RIA), a Western blot assay, or a slot blot assay. These methods are described in, e.g., Harlow et al., Antibodies: A Laboratory Manual, Cold Spring Harbor Laboratory Press, 2nd ed., 1988.

EXAMPLES

The following examples describe some exemplary modes of making and practicing certain compositions that are described herein. It should be understood that these examples are for illustrative purposes only and are not meant to limit the scope of the compositions and methods described herein.

Example 1: Inverted Melt Formulation Method for Preparing Antigen-Containing Vesicles This example describes an inverted melt formulation method for preparing antigen-containing non-ionic surfactant vesicles (NISV). In Step 1, a 5:4:1 molar ratio of the following lipids: 1-monopalmitoyl glycerol (MPG), cholesterol (CHO) and dicetyl phosphate (DCP) was placed in a flat bottom 50 ml glass beaker, ensuring none of the powder stuck to the side of the glass beaker. The lipids were melted in a heated oil bath at about 120-125° C. for 10 minutes, with occasional swirling in the glass beaker covered with aluminum foil.

At this stage, a stock solution of inactivated antigen vaccine (Imovax® Rabies vaccine reconstituted as per manufacturer Sanofi Pasteur's instructions) was pre-incubated for 5-10 minutes at about 30-35° C. in a heated water bath. In Step 2, the resulting vaccine stock solution was homogenized at 8,000 rpm at 30-35° C., and the molten lipid mixture was added into the homogenizing vaccine stock solution (to give either a 6.25 mg/ml—test article 1 (TA 1), 12.5 mg/ml—test article 2 (TA 2) or 25 mg/ml—test article 3 (TA 3) total lipid concentration homogenate) and homogenization was continued for a further 30 seconds at about 30° C. The resulting liposomal suspension homogenate was transferred into a closed bottle and shaken for 30 minutes at 220±10 rpm and about 30-35° C. An equivalent volume of a 400 mM sucrose solution in WFI water was added to the shaken homogenate and the homogenate was further shaken for 5 minutes at 220±10 rpm at about 30-35° C. This mixture was aliquoted (0.5 ml aseptically transferred into sterile 2 cc vials sealed with a rubber stopper) and frozen at −78 to −82° C., then lyophilized and reconstituted with sterile water for injection (WFI) prior to use in thermostability studies or in vivo immunogenicity studies in animals.

Example 2: Thermostability Studies of Inverted Melt Method Formulated Antigen-Containing Vesicles To assess thermostability, NISVs were prepared as described in Example 1, and lyophilized aliquots were stored (prior to reconstitution) at two different thermal storage temperatures (5±3° C. and 40±2° C.). The freeze-dried Imovax® Rabies vaccine, used in this Study, is stable if stored in the refrigerator at 2° C. to 8° C.; while reconstituted vaccine is not stable and should be used immediately. The Imovax® Rabies vaccine is also not stable at elevated temperatures in either lyophilized or reconstituted forms. At specified times, stability samples were removed from the temperature chambers, reconstituted in WFI and analyzed by appearance, pH, microscopy, Zeta Potential, nanosizing and ELISA (antigen content). Vaccine controls (Test article 7 (TA 7)—unformulated lyophilized Imovax® Rabies vaccine) were stored as above but without addition of NISVs and were also tested.

Rabies antigen content in NISV formulations was determined by performing a sandwich ELISA assay. Prior to the ELISA analysis, samples and standards were extracted by adding an equal volume of 100 mM carbonate-bicarbonate buffer (pH 9.5) with 0.5% Triton X-100 and pipetting up and down 10 times. Briefly, each well of 96 well ELISA plates was coated overnight at 4° C. with rabies virus monoclonal antibody (Ms Mab to Rabies virus (4.2 mg/ml) ab1002, Abcam) diluted 1/2000 in 25 mM bicarbonate buffer pH 9.7. The next day the coating solution was removed and the plates were blocked (1-3 hours at 37° C.) with 5% FBS in 0.05% Tween 20 in PBS. After the incubation time, plates were washed six times in wash buffer (0.05% Tween 20 in PBS). Then four to eight 2-fold serial dilutions of each extracted sample and standard were prepared using 5% FBS in 0.05% Tween 20 in PBS. The extracted and diluted samples and standards were added to the 96 well ELISA plates and were incubated for 1.5 h at 37° C. The plates were washed six times in wash buffer and incubated for 1 h at 37° C. with primary antibody (1/500 dilution of ferret sera in blocking solution). The plates were washed six times in wash buffer and incubated for 1 h at 37° C. with a 1/10,000 dilution of a goat anti-ferret IgG-Fc HRP conjugated secondary antibody (Bethyl). The plates were washed six times and developed using TMB substrate for 10 min at room temperature. Stop solution was added to each well and absorbance was read at 450 nm within 1 hour using an ELISA plate reader (Bio-Rad).

In Table 2 in vitro antigen content results are shown for TA 1 (Imovax® Rabies vaccine formulated in 6.25 mg/ml total lipid concentration NISVs), TA 2 (Imovax® Rabies vaccine in 12.5 mg/ml total lipid concentration NISVs), TA 3 (Imovax® Rabies vaccine in 25 mg/ml total lipid concentration NISVs) and TA 7 (unformulated lyophilized Imovax® Rabies vaccine) stability samples stored at either 4° C. or 40° C. for 0, 5 or 9 months. (Percent antigen content reflects the ratio of antigen detected in extracts from NISVs relative to the initial amount of inactivated antigen vaccine used in the preparation of NISVs).

TABLE 2

| Test Article | 0 months | 5 months | 9 months |
| --- | --- | --- | --- |
| TA 1-4° C. | 71% | 78% | 79% |
| TA 1-40° C. | NA | 80% | 78% |
| TA 2-4° C. | 69% | 64% | 63% |
| TA 2-40° C. | NA | 65% | 65% |
| TA 3-4° C. | 65% | 39% | 43% |
| TA 3-40° C. | NA | 43% | 47% |
| TA 7-4° C. | 88% | 81% | 73% |
| TA 7-40° C. | NA | 75% | 60% |

As can be seen in Table 2 there is no difference in thermostability between 4° C. and 40° C. stored samples of the same test articles for up to 9 months but overall the higher lipid concentration NISVs formulations stored at both temperatures were found to have a lower in vitro antigen content.

In Table 3 is shown the in vitro antigen content loss between 4° C. and 40° C. stored samples for TA 1 (Imovax® Rabies vaccine formulated in 6.25 mg/ml total lipid concentration NISVs) and TA 7 (unformulated lyophilized Imovax® Rabies vaccine) stability samples stored at either 4° C. or 40° C. for 0, 5, 9 or 18 months.

TABLE 3

| Test Article | 0 months | 5 months | 9 months | 18 months |
| --- | --- | --- | --- | --- |
| TA 1 | 0% | 0% | 1.3% | 13.8% |
| TA 7 | 0% | 7.4% | 17.8% | 63.6% |

As can be seen in Table 3 no appreciable loss in antigen content occurred between the 4° C. and 40° C. stored NISVs formulated Rabies Imovax® vaccine (TA 1-6.25 mg/ml total lipid concentration NISVs) for up to 18 months indicative of thermostability; while TA 7 (unformulated Rabies vaccine) loses significant antigen content between the 4° C. and 40° C. stored samples at the same time points which indicates lack of thermostability.

In Table 4 is presented the physical-chemical data derived on testing NISVs formulated Imovax® Rabies vaccine (TA 1-6.25 mg/ml total lipid concentration NISVs stored for 18 months at 4° C. and 40° C.) versus unformulated Imovax® Rabies vaccine (TA 7 stored for 18 months at 4° C. and 40° C.).

TABLE 4

| Test Article | Z-Ave (d, nm) | PDI | Zeta Potential (mV) | Osmolality (mmol/kg) | pH |
| --- | --- | --- | --- | --- | --- |
| TA 1-4° C. | 1111 | 0.530 | −76.2 | 692 | 9.18 |
| TA 1-40° C. | 2126 | 0.790 | −60.0 | 690 | 9.33 |
| TA 7-4° C. | 18.83 | 0.741 | −20.6 | 288 | 9.24 |
| TA 7-40° C. | 17.42 | 0.508 | −16.6 | 299 | 9.33 |

As expected the Z-average and zeta potential were different between the two test articles as TA 1 was formulated to have lipid-based antigen-containing vesicles and TA 7 was the unformulated vaccine control that did not contain any vesicles. Also as expected the Osmolality between TA 1 and TA 7 was different due to TA 1 containing sucrose whereas TA 7 did not contain any sucrose. Test Articles stored at the two different temperatures did not show any significant differences in physical-chemical parameters when compared to the other similarly formulated test articles.

Example 3: In Vivo Animal Testing of Inverted Melt Method Formulated Antigen-Containing Vesicles Female Balb/C mice (6-8 weeks old; body weight 18 to 28 grams, Charles River Canada Inc.) were immunized (n=8) intramuscularly once on day 0 (with 0.1 ml of indicated vaccine samples). Pre-immunization and post-1st immunization blood samples were collected to assess humoral immune responses to formulated and unformulated Imovax® Rabies Vaccine. Humoral immune responses were determined by performing an IgG ELISA Serological Assay. An indirect ELISA was performed to assess anti-rabies specific IgG titres in immune serum. Briefly, each well of 96 well ELISA plates was coated overnight at 4° C. with rabies antigen (Imovax® Vaccine, Sanofi Pasteur) diluted 1/25 in 25 mM bicarbonate buffer pH 9.7. The next day the plates were washed with PBS containing 0.05% Tween 20 and then blocked (1 h at 37° C.) with 10% goat sera in PBS. After the incubation time, plates were washed six times in wash buffer (0.05% Tween 20 in PBS). Then four to eight 2-fold serial dilutions of each serum sample were prepared using 10% goat sera in PBS. The sample and the controls were added to the 96 well ELISA plates and were incubated for 1.5 h at 37° C. The plates were washed six times in wash buffer and incubated for 1 h at 37° C. with a 1/5000 dilution of a goat anti-mouse IgG-Fc HRP conjugated secondary antibody (Bethyl). The plates were washed six times and developed using TMB substrate for 3 min at room temperature. Absorbance was read at 450 nm with an ELISA plate reader (Bio-Rad). The inverted end point titre is considered the highest sera dilution for which the OD450 reading is higher or equal with 0.1. Results on Geometric Mean (GM) of OD450 reading of 1/800 dilution of serum samples are presented in Table 5 for Imovax® Rabies Vaccine formulated with lipids as described previously versus unformulated Imovax® Rabies Vaccine.

TABLE 5

| Test Article Group (n = 8) | Storage Temp | Antigen Dose (IU/volume) | Formulation Method | Total Lipid | Homogenization | GM of OD450 of 1/800 Serum Dilution) |
|---|---|---|---|---|---|---|
| TA 1 | 4° C. | Imovax® Rabies (0.25 IU/100 μL) | Inverted Melt with Sucrose | 6.25 mg | 30 sec at 8,000 rpm | 0.77 |
| TA 7 | 4° C. | Imovax® Rabies (0.25 IU/100 μL) | Commercial Formulation | — | — | 0.43 |

The GM of OD450 reading for a 1/800 serum dilution of TA 1 (Imovax® Rabies Vaccine formulated with 6.25 mg/ml total lipid concentration NISVs stored at 4° C. for 18 months) was significantly higher than the GM of OD450 reading for a 1/800 serum dilution of TA 7 (unformulated Imovax® Rabies Vaccine stored at 4° C. for 18 months) indicating that the inverted melt non-ionic surfactant (NISVs) lipid based formulation appeared to have an adjuvant effect on the Rabies Vaccine.

Other Embodiments

Other embodiments of the disclosure will be apparent to those skilled in the art from a consideration of the specification or practice of the disclosure disclosed herein. It is intended that the specification and examples be considered as exemplary only, with the true scope of the disclosure being indicated by the following claims. The contents of any reference that is referred to herein are hereby incorporated by reference in their entirety.

What is claimed is:

1. A method of preparing a thermostable lyophilized composition comprising (i) an inactivated viral antigen, said antigen comprising an inactivated polio virus, an inactivated rabies virus, an inactivated hepatitis A virus, or a combination thereof and (ii) lipid vesicles, wherein the lipid vesicles comprise a non-ionic surfactant comprising 1-monopalmitoyl glycerol, the method comprising:

melting lipids comprising the non-ionic surfactant to produce molten lipids;

combining the molten lipids with an aqueous solution comprising the inactivated viral antigen;

homogenizing the resulting product, wherein the molten lipids and aqueous solution are combined in relative amounts and volumes that achieve a lipid concentration of about 6.25 mg/ml to about 25 mg/ml in the resulting product; and lyophilizing the homogenized mixture to produce the lyophilized composition, wherein the lyophilized composition is thermostable when stored for a period of up to nine months at a temperature of 8° C. to 40° C.

2. The method of claim 1, wherein the molten lipids are added to the aqueous solution.

3. The method of claim 1, wherein the aqueous solution is added to the molten lipids.

4. The method of claim 1, wherein the lyophilized composition is thermostable when stored for a period of up to nine months at a temperature of 8° C. to 25° C.

5. The method of claim 1, wherein the thermostable lyophilized composition, when stored for a period of up to nine months at a temperature of 8° C. to 40° C., exhibits a lower level of antigen loss relative to a corresponding composition comprising the antigen and lacking lipid vesicles.

6. The method of claim 4, wherein the thermostable lyophilized composition, when stored for a period of up to nine months at a temperature of 8° C. to 25° C., exhibits a lower level of antigen loss relative to a corresponding composition comprising the antigen and lacking lipid vesicles.

7. A method of treating an individual suffering from, or at risk for, infection from a polio virus, a rabies virus, a hepatitis A virus or a combination thereof, the method comprising:

a) melting lipids comprising a non-ionic surfactant comprising 1-monopalmitoyl glycerol to produce molten lipids;

combining the molten lipids with an aqueous solution comprising an inactivated polio virus, an inactivated rabies virus, an inactivated hepatitis A virus, or a combination thereof;

homogenizing the resulting product to produce a homogenized mixture, wherein the molten lipids and aqueous solution are combined in relative amounts and volumes that achieve a lipid concentration of about 6.25 mg/ml to about 25 mg/ml in the homogenized mixture;

b) lyophilizing the homogenized mixture to produce a lyophilized composition, wherein the lyophilized composition is thermostable when stored for a period of time at a temperature in excess of 8° C.;

c) rehydrating the lyophilized composition with an aqueous solution to form a rehydrated composition comprising a vesicle comprising 1-monopalmitoyl glycerol and the inactivated polio virus, the inactivated rabies virus, the inactivated hepatitis A virus, or the combination thereof; and d) administering to the individual a therapeutically effective amount of the rehydrated composition.

8. The method of claim 7, wherein the lyophilized composition is thermostable when stored for a period of time at a temperature in excess of 25° C.

9. The method of claim 7, wherein the lyophilized composition is thermostable when stored for a period of time at a temperature in excess of 30° C.

10. The method of claim 7, wherein the lyophilized composition is thermostable when stored for a period of time at a temperature in excess of 35° C.

11. The method of claim 7, wherein the composition is administered by intramuscular injection.

12. The method of claim 7, wherein the composition is administered by subcutaneous injection.

13. The method of claim 7, wherein the composition elicits an immune response in the individual at a first level that is higher than a second level of an immune response elicited by a second composition comprising the inactivated polio virus, the inactivated rabies virus, the inactivated hepatitis A virus, or the combination thereof and lacking the vesicle.

* * * * *